United States Patent [19]

Hickmann

[11] Patent Number: 4,734,499

[45] Date of Patent: Mar. 29, 1988

[54] PREPARATION OF α,β-DIAMINOACRYLONITRILES

[75] Inventor: Eckhard Hickmann, Dannstadt-Schauernheim, Fed. Rep. of Germany

[73] Assignee: BASF Aktiengesellschaft, Ludwigshafen, Fed. Rep. of Germany

[21] Appl. No.: 777,931

[22] Filed: Sep. 19, 1985

[30] Foreign Application Priority Data

Sep. 20, 1984 [DE] Fed. Rep. of Germany ....... 3434525

[51] Int. Cl.$^4$ ................. C07D 243/08; C07D 241/06; C07C 121/30
[52] U.S. Cl. .................................... 540/575; 544/336; 546/186; 548/524; 558/332
[58] Field of Search .................. 544/336; 558/332; 546/186; 548/524; 540/575

[56] References Cited

FOREIGN PATENT DOCUMENTS 0072953 5/1982 Japan .

OTHER PUBLICATIONS

Otsuka, et al., Chemistry Letters, pp. 939–942 (1972).
H. Böhme and K. H. Weisel, Chem. Ber. 109 (1976), 1908.
Deyrup, et al., Synthesis, pp. 34–36, (1974).
Hinsberg Oxindole Synthesis, Merck Index 10th Edition (1983), p. ONR-43.
Strecker Synthesis, Merck Index 10th Edition (1983) p. ONR-87.

*Primary Examiner*—Donald G. Daus
*Assistant Examiner*—William A. Teoli, Jr.
*Attorney, Agent, or Firm*—John H. Shurtleff

[57] ABSTRACT

α,β-Diaminoacrylonitriles of the general formula I $$R^3R^2NC(R^1)=C(NR^2R^3)CN \qquad I$$

where $R^1$, $R^2$ and $R^3$ are identical or different and independently of one another are each hydrogen, alkyl, cycloalkyl, aralkyl, aryl or a heterocyclic radical, and the organic radicals $R^2$ may furthermore be bonded to one another to form a 6-membered or 7-membered ring, or $R^2$ and $R^3$ may be bonded to one another to form a 5-membered or 6-membered ring, are prepared by reacting an α-dicarbonyl compound $R^1COCHO$, or a reactive derivative of this with (a) a salt of sulfurous acid or sulfur dioxide, (b) an amine $HNR^2R^3$ or an aliphatic diamine $R^3HN\text{-}(CH_2)_nNHR_3$ where n is 2 or 3 and (c) hydrocyanic acid or a hydrocyanic acid donor in any sequence.

12 Claims, No Drawings

PREPARATION OF α,β-DIAMINOACRYLONITRILES

The present invention relates to a novel process for the preparation of α,β-diaminoacrylonitriles of the general formula I $$R^3R^2NC(R^1)=C(NR^2R^3)CN \qquad I$$

where $R^1$, $R^2$ and $R^3$ are identical or different and independently of one another are each hydrogen, alkyl, cycloalkyl, aralkyl, aryl or a heterocyclic radical, and the organic radicals $R^2$ may furthermore be bonded to one another to form a 6-membered or 7-membered ring, or $R^2$ and $R^3$ may be bonded to one another to form a 5-membered or 6-membered ring.

It has been disclosed that 2,3-di-tert.-butylamino- and 2,3-di-tert.-butylamino-3-phenyl-crotononitrile can be prepared by decomposing nickel isocyanide complexes (Chem. Lett. 939, 1972). However, the small yield of only 5–20% obtained in this reaction does not permit its use for preparative purposes.

According to H. Böhme and K. H. Weisel (Chem. Ber. 109 (1976), 1908), 3-arylamino-2-halocrotononitrile can be converted to the α,β-diaminocrotononitriles by exchanging halogen for a dialkylamino group. This method can only be used for the preparation of α,β-diaminoacrylonitrile whose β-amino group is aryl-substituted and in which $R^1$ is methyl.

Furthermore, Synthesis 35, 1974, states that α,β-diaminoacrylonitriles can be prepared by reacting a glyoxaldiimine with acetone cyanohydrin. Compounds in which $R^1$ is H or p-$NO_2$—$C_6H_4$, $R^2$ is H and $R^3$ is tert.butyl or ortho-toluidino have been prepared by this route.

This method too is not applicable generally. For example, it does not permit the synthesis of 1,4,5,6-tetrahydro-2-cyanopyrazine (TCP) which is unknown to date and is of particular industrial importance.

It is an object of the present invention to provide a novel process for the preparation of α,β-diaminoacrylonitrile which permits the radicals $R^1$, $R^2$ and $R^3$ to be varied over a wide range.

We have found that this object is achieved by a novel process for the preparation of α,β-diaminoacrylonitriles of the general formula I $$R^3R^2NC(R^1)=C(NR^2R^3)CN \qquad I$$

where $R^1$, $R^2$ and $R^3$ are identical or different and independently of one another are each hydrogen, alkyl, cycloalkyl, aralkyl, aryl or a heterocyclic radical, and the organic radicals $R^2$ may furthermore be bonded to one another to form a 6-membered or 7-membered ring, or $R^2$ and $R^3$ may be bonded to one another to form a 5-membered or 6-membered ring, wherein component (A) is reacted with components (B), (C) and (D), i.e.

(A) an α-dicarbonyl compound of the general formula $R^1COCHO$, where $R^1$ has the above meanings, or a reactive derivative of this carbonyl compound, (B) a salt of sulfurous acid or sulfur dioxide or a sulfur dioxide donor, (C) an amine of the general formula $HNR^2R^3$, or an aliphatic diamine of the general formula $R^3HN-(CH_2)_n-NHR^3$, where n is 2 or 3, the alkylene chain may carry a further substituent $R^1$, and $R^1$ and $R^3$ have the above meanings, or a derivative which is converted to the amine or diamine under the reaction conditions, and (D) liquid or gaseous hydrocyanic acid or a hydrocyanic acid donor, in any sequence.

(A)+(B)+(C)+(D) react in accordance with the following equation:

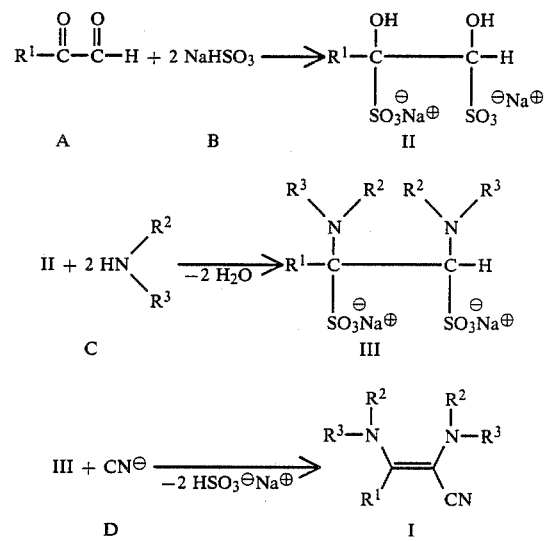

Components (A)–(D) may be combined in any sequence; it is also possible to combine 2 or more components simultaneously, or to react a mixture of 2 or more components with the remaining components in any manner. The synthesis of I can be carried out by a single-vessel process, or any intermediate, e.g. the disodium salts of the bis-α-hydroxysulfonic acid II or of the bis-α-aminosulfonic acid III, may be isolated and reacted further with the remaining reactant or reactants to give I.

The fact that this process is successful is surprising since it is known that components (A), (B) and (C) are capable of reacting with one another at elevated temperatures, giving oxindoles when secondary amines are used, or open-chain or cyclic glycinamides when monoamines or α,β- or α,β-diamines are used as starting materials (cf. Hinsberg Oxindole Synthesis, Merck Index 10th edition 1983, page ONR-43).

The proportions of components (A), (B), (C) and (D) can be varied within wide limits. For reasons of cost effectiveness, the amounts used should as a rule correspond fairly closely to a molar ratio, i.e. A:B:C:D ≈ 1:2:2/1 (monoamine/diamine):1.

However, it is often advantageous to employ (B) in excess, e.g. in a ratio of A:B from 1:2 to 1:4. (C) too can in many cases advantageously be used in excess, e.g. A:C=1:2 to 1:5/10 (monoamine/diamine). (D) too may be used in excess, e.g. A:D=1:1 to 1:3, without having to accept a loss of yield of the desired product I. This result is unexpected since, in analogy to the Strecker aminonitrile synthesis from monocarbonyl compounds, as modified by Bucherer and Knoevenagel (cf. The Merck Index, 10th edition, 1983, page ONR-87), the reaction of α-dicarbonyl compounds ($R^1COCHO$) with amines ($HNR^2R^3$) by the Strecker method would have been expected to lead to bis-(α-aminonitriles) of the general formula $R^3R^2NCR^1(CN)$-$CH(CN)NR^2R^3$.

In the novel process, α-dicarbonyl compounds of the general formula $R^1COCHO$ are used. $R^1$ is, for example, hydrogen, a branched or straight-chain aliphatic radical of 1 to 30, preferably 1 to 10, in particular 1 to 5, carbon atoms, a cycloaliphatic radical possessing 3 to 8 ring members, an aromatic or heteroaromatic radical or an araliphatic radical of 7 to 12 carbon atoms.

The stated organic radicals may furthermore be substituted by groups which are inert under the reaction conditions, e.g. nitro or alkoxy.

The α-dicarbonyl compound can be used directly or in the form of a reactive derivative, e.g. an oligomer or polymer, a hydrate, a hemiacetal, an acetal, an enol ester, an aminal or a diimine. Advantageously, it is reacted in the form of one of the intermediates occurring under the reaction conditions, e.g. as a bisulfite adduct, a cyanohydrin, a bis-α-aminosulfonic acid or one of its salts, or an open-chain or cyclic diimine. In addition to the glyoxal derivatives, glyoxal itself may be particularly advantageously used.

Gaseous or liquid sulfur dioxide, and especially a sulfurous acid salt which can also be produced in situ from other salts, e.g. from disulfites or from sulfur dioxide and a base, can be used as component (B). Suitable salts of sulfurous acid are alkali metal disulfites, sulfites and in particular bisulfites, e.g. sodium bisulfite.

Suitable components (C) are amines of the general formula $R^2R^3NH$, where $R^2$ and $R^3$ are identical or different and are each hydrogen, a branched or straight-chain aliphatic radical of 1 to 15, preferably 1 to 10, in particular 1 to 5, carbon atoms, a cycloaliphatic radical possessing 3 to 8 ring members, an aromatic or heterocyclic radical or an araliphatic radical of 7 to 12 carbon atoms, e.g. methyl-, ethyl-, propyl-, isopropyl-, butyl-, tert.-butyl-, cyclohexyl-or benzylamine or aniline and dimethyl-, diethyl- or diisopropylamine or methylaniline.

The radicals $R^2$ and $R^3$ may furthermore be bonded to one another to form a 5-membered or 6-membered ring, which may carry a further hetero atom, e.g. piperidine, pyrrolidine or morpholine. Particularly important with regard to the synthesis of 1,4,5,6-tetrahydro-2-cyanopyrazines are aliphatic diamines where the alkylene chain is of 2 carbon atoms, e.g. ethylenediamine. The alkylene chain can, if desired, carry a further substituent $R^1$, as in, for example, propane-1,2-diamine.

As a rule the amines are reacted directly, but may also be used in the form of their salts, complexes or hydrolyzable derivatives.

The novel process is generally used for the preparation of α,β-diaminoacrylonitriles having two identical amino groups; however, it is also possible to synthesize those which possess different amine substituents and in which the two radicals $R^2$ and/or the two radicals $R^3$ differ.

Liquid or gaseous hydrocyanic acid or a hydrocyanic acid donor can be used as component (D). Suitable hydrocyanic acid donors are (a) a complex capable of undergoing dissociation, (b) an adduct of hydrocyanic acid, e.g. a cyanohydrin, advantageously the cyanohydrin of the α-dicarbonyl compound used, (c) a solvolysis of a hydrocyanic acid derivative, e.g. an acid cyanide or a silyl cyanide, which takes place with formation of hydrocyanic acid or a cyanide, and in particular (d) a salt, e.g. sodium cyanide.

The reaction of components (A) to (D) can be carried out in the absence of a solvent or in an excess of one of the components, or a mixture of the components, as a solvent. However, the reaction is advantageously carried out in a solvent or solvent mixture. Possible solvents are alcohols, ketones, esters, nitriles, amides and other polar aprotic solvents, e.g. dimethylformamide, tetramethylurea and dimethyl sulfoxide. Water is particularly suitable, either as the sole solvent or as the principal component of a solvent mixture.

In the preferred embodiment, the α,β-diaminoacrylonitriles are prepared without isolation of intermediates. However, an intermediate may be isolated at any point, for example the bisulfite adduct formed from (A) and (B), or the bis-α-aminosulfonic acid, or the bis-α-aminosulfonic. acid formed from (A), (B) and (C) or a salt of this, usually a hydrated salt, and can be reacted further under suitable reaction conditions. This procedure is appropriate when it is advantageous to change the solvent in the course of reacting the reactants (A), (B), (C) and (D).

Frequently, the addition of a base, e.g. sodium hydroxide solution or an amine, in particular an excess, over and above the stoichiometric amount, of the amine or diamine employed, during the reaction or prior to working up results in a substantial increase in yield.

The reaction can be carried out under reduced pressure, superatmospheric pressure or atmospheric pressure, either batchwise or continuously.

In general, very mild temperature conditions are chosen. The reaction temperature is preferably from 0° to 100° C., in particular from 0° to 50° C. In order completely or substantially to dissolve any resulting precipitate after the reaction of components (A), (B) and (C), it is as a rule advisable to heat the reaction mixture for a short time to 40°-80° C. after the final component has been added. Reactant (D) is advantageously added at a fairly low temperature, e.g. from 0° to 30° C.

The desired product I is isolated by a conventional method, for example by sedimentation, by means of a hydrocyclone, by filtration, by centrifuging or in particular by extraction.

Extraction can be carried out uSing any organic solvent which possesses limited solubility in water, at least in the presence of salts. Organic solvents which exhibit limited solubility in water and carry polar groups, e.g. alcohols of 4 or more carbon atoms, dialkyl ethers, aryl alkyl ethers, ketones of 4 or more carbon atoms, carboxylates, carboxylic acids of 5 or more carbon atoms, nitriles of 4 or more carbon atoms, and amides of 5 or more carbon atoms, are particularly suitable. As a rule, the extracting agent is added only after the reaction is complete, but may be introduced during the reaction or initially taken at the very beginning.

The α,β-diaminoacrylonitriles which can be prepared by the novel process are useful, inter alia, as intermediates for the preparation of drugs, crop protection agents, dyes and assistants. Where one of the radicals $R^2$ and $R^3$ is hydrogen, the said compounds can be dehydrated, cyclic, six-membered α,β-diaminoacrylonitriles giving pyrazine derivatives. For example, treatment of 1,4,5,6-tetrahydro-2-cyanopyrazine with nickel peroxide gives pyrazinecarboxamide, which is used as a component in antitubercular combination preparations.

In the Examples which follow, parts bear the same relation to parts by volume as that of the kilogram to the liter.

EXAMPLE 1

1210 parts of 38% strength $NaHSO_3$ solution are initially taken, 290 parts of 40% strength glyoxal solution are metered in at from 20° to 40° C., 120 parts of ethylenediamine are added at from 20° to 30° C. and the mixture is heated at about 50° C. for 30 minutes. 406 parts of 30% strength aqueous NaCN solution are run into the solution, which has been cooled to 0°–5° C., and stirring is continued for a further hour. About 150 ml of 50% strength sodium hydroxide solution are then added, the reaction mixture warming up to about 45° C. When the mixture is extracted twice with 2000 parts by volume of methyl ethyl ketone in each case and the combined extracts are evaporated down, 186 parts (85% of theory) of 1,4,5,6-tetrahydro-2-cyanopyrazine (TCP) are obtained, the product being pure according to thin layer chromatography. After recrystallization from methanol, the product melts at 96°–98° C.

Elemental analysis of the product: Found: C: 54.8%; H: 6.5%; N: 38.7% Calculated for $C_5H_7N_3$: C: 55.0%; H: 6.5%; N: 38.5%

The mass spectrum of the product exhibits the molecular peak at m/e=109. The IR spectrum of a KBr pellet of the substance shows, inter alia, the following characteristic band maxima (in $cm^{-1}$): 3276 (s), 3216 (m), 3060 (w), 2719 (s), 1622 (s), 1517 (m), 1343 (m), 1268 (m), 858 (m), 809 (m).

In the NMR spectrum (dilute solution in DDMSO, TMS as internal standard, chemical shift in ppm), the following bands appear: about 2.8 (multiplet, 2 H), about 3.0 (multiplet, 2 H), about 3.6 (broad triplet, 1 H), about 6.1 (broad multiplet, 1 H), about 6.55 (doublet, 1 H).

EXAMPLE 2

275 parts of 38% strength $NaHSO_3$ solution, 72.5 parts of 40% strength glyoxal solution, 30 parts of ethylenediamine and 106 parts of 30% strength aqueous NaCN solution are reacted as described in Example 1, except that the treatment with sodium hydroxide solution is omitted, and the product is extracted continuously for hours with methyl tert.-butyl ether. When the organic phase is separated off and evaporated down, 24 parts (44% of theory) of analytically pure 1,4,5,6-tetrahydro-2-cyanopyrazine are obtained.

EXAMPLE 3

68.75 parts of 38% strength $NaHSO_3$ solution, 14.5 parts of 40% strength glyoxal solution, 6 parts of ethylenediamine and 45.4 parts of 30% strength aqueous NaCN solution and 8 parts of 50% strength sodium hydroxide solution are reacted as described in Example 1. When the mixture is extracted first with 300 parts by volume and then with 150 parts by volume of methyl ethyl ketone and the combined extracts are evaporated down, 88.3 parts (81% of theory) of 1,4,5,6-tetrahydro-2-cyanopyrazine are obtained, the product being pure according to thin layer chromatography.

EXAMPLE 4

55 parts of 38% strength $NaHSO_3$ solution are initially taken, 14.5 parts of 40% strength aqueous glyoxal solution are added at from 20° to 40° C., the mixture is stirred for about a further ½ hour and then cooled to 0° C., 22.7 parts of 30% strength aqueous NaCN solution are added, stirring is continued for about a further ½ hour, 6 parts of ethylenediamine are added at from 0° to 14° C., the mixture is heated for a short time at 50° C. and then cooled to room temperature, stirring is continued for about 2 hours, 16 parts of 50% strength aqueous sodium hydroxide solution are added, the mixture is extracted with twice 300 parts by volume of methyl ethyl ketone and the combined extracts are evaporated down. 7.0 parts (64% of theory) of 1,4,5,6-tetrahydro-2-cyanopyrazine are obtained, the product being pure according to thin layer chromatography.

EXAMPLE 5

55 parts of 38% strength $NaHSO_3$ solution are initially taken at 0° C., 22.7 parts of 30% strength aqueous NaCN solution are added at from 0° to 10° C., the mixture is stirred for a further 15 minutes, 6 parts of ethylenediamine are added at from 0° to 16° C., stirring is continued for a further 15 minutes, 14.5 parts of 40% strength aqueous glyoxal solution are added at from 0° to 10° C., the mixture is heated for a short time at about 50° C., stirring is continued for about a further 2 hours at room temperature, 16 parts of 50% strength aqueous sodium hydroxide solution are added and extraction is carried out as described in Example 4. 6.3 parts (58% of theory) of 1,4,5,6-tetrahydro-2-cyanopyrazine are obtained, the product being pure according to thin layer chromatography.

EXAMPLE 6

6 parts of ethylenediamine are initially taken, 55 parts of 38% strength aqueous $NaHSO_3$ solution are added at room temperature, the mixture is stirred for a further 15 minutes, 14.5 parts of 40% strength aqueous glyoxal solution are added, stirring is continued for a further 15 minutes, 22.7 parts of 30% strength aqueous NaCN solution are added at from 0° to 12° C., the mixture is heated for a short time at 50° C., stirring is continued for a further 2 hours at room temperature, 16 parts of 50% strength aqueous sodium hydroxide solution are added and working up is carried out as described under Example 4. 7.8 parts (72% of theory) of 1,4,5,6-tetrahydro-2-cyanopyrazine are obtained, the product being pure according to thin layer chromatography.

EXAMPLE 7

14.5 parts of 40% strength aqueous glyoxal solution are initially taken, 6 parts of ethylenediamine are added at from 0° to 10° C., the mixture is stirred for a further 15 minutes, 55 parts of 38% strength $NaHSO_3$ solution are added at from 5° to 10° C., 22.7 parts of 30% strength aqueous NaCN solution are added at from −5° to 0° C., the mixture is heated for a short time at 50° C., stirring is continued for a further 2 hours at room temperature, 16 parts of 50% strength aqueous sodium hydroxide solution are added and working up is carried out as described under Example 4. 4.9 parts (45% of theory) of 1,4,5,6-tetrahydro-2-cyanopyrazine are obtained, the product being pure according to thin layer chromatography.

EXAMPLE 8

300 parts by volume of methyl ethyl ketone are initially taken, 55 parts of 38% strength aqueous $NaHSO_3$ solution are added, 14.5 parts of 40% strength aqueous glyoxal solution are introduced at from 20° to 30° C., the mixture is stirred for a further 15 minutes, 6 parts of ethylenediamine are added at from 20° to 40° C., stirring is continued for a further 30 minutes, the mixture is cooled to 0° C., 5.1 parts of solid NaCN are added, stirring is continued for 10 minutes, the solution is heated to 50° C., stirring is continued for a further 2 hours, 16 parts of 50% strength aqueous sodium hydroxide solution are added and the organic phase is separated off. The aqueous phase is extracted with a further 300 parts by volume of methyl ethyl ketone, and the combined organic phases are evaporated down. 8.8 parts (81% of theory) of 1,4,5,6-tetrahydro-2-cyanopyrazine are obtained, the product being pure according to thin layer chromatography.

EXAMPLE 9

275 parts of 38% strength aqueous $NaHSO_3$ solution are initially taken, 72.5 parts of 40% strength aqueous gly-oxal solution are added at from 20° to 30° C., the mixture is stirred for a further 30 minutes, 30 parts of ethylene-diamine are introduced at from 15° to 25° C. and the stirred solution is heated at about 60° C. until the precipitate initially formed has substantially gone into solution. The resulting solution is stirred into about 2000 parts by volume of methanol, and the yellow precipitate which separates out is filtered off under suction and dried for 2 days at about 40° C. under reduced pressure from a water pump. 124 parts (75% of theory) of disodium piperazine-2,3-disulfonate dihydrate are obtained, the product having the following elemental composition:

C: 14.5%; H: 3.4%; N: 7.8%; Na: 15.1%; O: 39.7%; S: 19.6% Calculated composition for $C_4H_8N_2Na_2O_6S_2$. 2 $H_2O$: C: 14.9%; H: 3.7%; N: 7.5%; Na: 14.3%; O: 39.8%; S: 19.9%

The water content of the product is determined as 11.6% (calculated: 11.2%).

If 35 parts of aqueous 37% strength hydrochloric acid are added to 100 parts of the disodium salt described above, the resulting precipitate is filtered off under suction and washed with distilled water, and the chloride-free residue is dried under reduced pressure from an oil pump, 37 parts (54% of theory) of piperazine-2,3-disulfonic acid monohydrate of melting point 124°–126° C. are obtained. The product has the following elemental composition:

C: 18.1%; H: 4.7%; N: 10.5%; O: 42.5%, S: 24.1% Calculated for $C_4H_{10}N_2O_6S_2$. $H_2O$: C: 18.2%; H: 4.6%; N: 10.6%; O: 42.4%; S: 24.2%

145 parts of the disodium salt described above in 450 parts by volume of water are initially taken, the solution is cooled to −4° C., a solution of 26 parts of 95% pure NaCN in 87.5 parts by volume of water is added at this temperature, and the mixture is stirred for a further 2 hours at 0° C. and worked up as described in Example 4. 16.6 parts (34% of theory) of 1,4,5,6-tetrahydro-2-cyanopyrazine are obtained, the product being pure according to thin layer chromatography.

EXAMPLE 10

72.5 parts of 40% strength aqueous glyoxal solution are initially taken and diluted with about 200 parts by volume of water, 64 parts of gaseous sulfur dioxide are passed in at from 20° to 35° C. and 30 parts of ethylene-diamine are added, an orange precipitate separating out in a clearly exothermic reaction. The product is filtered off under suction, washed with water and dried at about 70° C. under reduced pressure from a water pump. 100 parts (71% of theory) of a yellowish product (ethylenediammonium salt of 1,2-dihydroxyethane-1,2-disulfonic acid? ) having the following empirical elemental composition are obtained:

C: 17.5%; H: 5.2%; N: 10.2%; O: 44.5%; S: 22.0% Calculated for $C_4H_{14}N_2O_8S_2$ C: 17.0%; H: 5.0%; N: 9.9%; O: 45.4%; S: 22.7%

If 56.4 parts of the product described above are neutralized with 32 parts of 50% strength aqueous sodium hydroxide solution and the procedure is continued as described in Example 9, 12.7 parts (58% of theory) of 1,4,5,6-tetrahydro-2-cyanopyrazine are obtained, the product being pure according to thin layer chromatography.

EXAMPLE 11

16.8 parts of the diimine obtained from glyoxal and tert.-butylamine (1,4-di-tert.-butyl-1,4-diaza-1,3-butadiene) are suspended in 50 parts by volume of water, 82.5 parts of 38% strength aqueous $NaHSO_3$ solution are added at from 20° to 40° C., the mixture is stirred for a further 2 hours, 6 parts of ethylenediamine are introduced at from 20° to 35° C., stirring is continued for a further 8 hours, the mixture is cooled to −4° C., a solution of 5.2 parts of 95% pure NaCN in 17.5 parts by volume of water is added, stirring is continued for 8 hours, the pH is brought to 12.4 by adding 50% strength aqueous sodium hydroxide solution, and working up is carried out as described under Example 4. 7 parts (64% of theory) of 1,4,5,6-tetrahydro-2-cyanopyrazine are obtained, the product being pure according to thin layer chromatography.

EXAMPLE 12

12 parts of ethylenediamine in 100 parts by volume of dimethylformamide are initially taken, 54.2 parts of a glyoxal/sodium bisulfite adduct are metered in at about 20° C., the mixture is stirred for a further 4 hours at from 20° to 30° C., 10.4 parts of 95% pure NaCN are added at about 0° C., the mixture is stirred for 8 hours at about 20° C., the solution is filtered off from the precipitate, and the solvent is distilled off under reduced pressure from an oil pump to give 12 parts (55% of theory) of a dark residue which, according to thin layer chromatography, substantially consists of 1,4,5,6-tetrahydro-2-cyanopyrazine.

EXAMPLE 13

13.8 parts of phenylglyoxal and 40 parts by volume of water are initially taken and heated to about 50° C., 61 parts of 38% strength aqueous $NaHSO_3$ solution are introduced, and methanol is added in an amount sufficient to dissolve virtually all solid material. Thereafter, 6 parts of ethylenediamine are added at about 30° C., the mixture is heated at 50° C. for 30 minutes and then cooled to about 10° C., a solution of 5.2 parts of 95% pure NaCN in 13 parts by volume of water is added at this temperature, stirring is continued for a further 2 hours at room temperature and working up is carried out as described under Example 4. 10 parts (54% of theory) of 1,4,5,6-tetrahydro-3-phenyl-2-cyanopyrazine are obtained in the form of a reddish brown, viscous oil. The mass spectrum of this product shows the molecular peak expected for the empirical formula $C_{11}H_{11}N_3$, at e/m=185, and its NMR spectrum exhibits the bands typical of the different NH groups, at about 3.5 ppm ($N^1$-H) and about 6.15 ppm ($N^4$-H).

EXAMPLE 14

330 parts of 38% strength aqueous $NaHSO_3$ solution are initially taken, 72.5 parts of 40% strength aqueous glyoxal solution are added, 94 parts of aniline are introduced, the mixture is heated at about 50° C. for 30 minutes and then cooled to room temperature, and 80 parts of 50% strength aqueous sodium hydroxide solution are added, followed by a solution of 26 parts of 95% pure NaCN in 60 parts by volume of water at about 15° C. Stirring is continued for 2 hours at room temperature, the mixture is extracted with methyl ethyl ketone as described under Example 4 and the organic phase is evaporated down to give 190 parts of crude product. For further purification, the crude product is extracted twice with about 300 parts by volume of methyl tert.-butyl ether in each case, and the combined extracts are evaporated down. 70 parts (30% of theory) of $\alpha,\beta$-dianilinoacrylonitrile are obtained. The mass spectrum of the product exhibits the molecular peak expected for the empirical formula $C_{15}H_{13}N_3$, at $m/e=235$, and its NMR spectrum shows the bands typical of the different NH groups, at about 3.35 ppm ($N^1$-H) and about 5.0 ppm ($N^4$-H).

EXAMPLE 15

200 parts of nickel peroxide (freshly prepared from nickel sulfate hexahydrate and sodium hypochlorite solution containing sodium hydroxide solution, and dried under reduced pressure) in 600 parts by volume of benzene are initially taken, 11 parts of 1,4,5,6-tetrahydro-2-cyanopyrazine are added and the mixture is refluxed for 3 hours. The virtually colorless liquid phase is filtered off, and the filtration residue is digested with methanol. Evaporating down the methanolic solution gives 2 parts ($\cong$18% of theory) of pyrazinecarboxamide.

We claim:

1. A process for the preparation of an $\alpha,\beta$-diaminoacrylonitrile of the formula $$R^3R^2NC(R^1)=C(NR^2R^3)CN \qquad I$$

where $R^1$, $R^2$ and $R^3$ are identical or different and independently of one another are each hydrogen or an organic group selected from the class consisting of alkyl, cycloalkyl, aralkyl of 7 to 12 carbon atoms or phenyl, each of said organic groups being unsubstituted or substituted by an inert group selected from the class consisting of nitro and alkoxy, and the organic radicals $R^2$ may furthermore be bonded to one another to form a 6-membered or 7-membered heterocyclic ring, or $R^2$ and $R^3$ may be bonded to one another to form a 5-membered or 6-membered heterocyclic ring, which process comprises reacting in any sequence the component (A) with the components (B), (C) and (D) as follows:

(A) an $\alpha$-dicarbonyl compound of the formula $R^1CO$-CHO, where $R^1$ has the above meanings, or a derivative which is converted to this carbonyl compound under the reaction conditions, (B) a salt of sulfurous acid or sulfur dioxide or a donor reagent which liberates sulfur dioxide under the reaction conditions, (C) an amine of the formula $HNR^2R^3$, or an aliphatic diamine of the formula $R^3HN-(CH_2)_n13\ NHR^3$, where the alkylene chain may carry a further substituent $R^1$, $R^1$ and $R^3$ having the above meanings and n being 2 or 3, or a derivative which is converted to such amine or diamine under the reaction conditions, and (D) liquid or gaseous hydrocyanic acid or a donor reagent which liberates hydrocyanic acid under the reaction conditions.

2. A process as claimed in claim 1, wherein the $\alpha$-dicarbonyl compound is used in the form of a bisulfite adduct or of a cyanohydrin.

3. A process as claimed in claim 1, wherein the $\alpha$-dicarbonyl compound is used in the form of a bis-$\alpha$-aminosulfonic acid or of one of its salts.

4. A process as claimed in claim 1, wherein the $\alpha$-dicarbonyl compound is used in the form of an open-chain or cyclic diimine.

5. A process as claimed in claim 1, wherein the $\alpha$-dicarbonyl compound is glyoxal, a glyoxal oligomer or polymer or a glyoxal derivative.

6. A process as claimed in claim 1, wherein an alkali metal bisulfite or sulfite or an alkali metal disulfite is used as the salt of sulfurous acid.

7. A process as claimed in claim 1, wherein the amine component used is ethylene diamine.

8. A process as claimed in claim 1, wherein the hydrocyanic acid donor used is an alkali metal cyanide or a cyanohydrin.

9. A process as claimed in claim 1, wherein the reactions are carried out in predominantly aqueous solution.

10. A process as claimed in claim 1, wherein component (A) is reacted with reactants (B) and (C) at from 0° to 100° C., and component (D) is added at from 0° to 30° C.

11. A process as claimed in claim 1, wherein either the reaction is carried out without isolation of intermediates, or an intermediate is isolated and is reacted further in a solvent or solvent mixture other than that used previously.

12. A process as claimed in claim 1, wherein the product of the formula I is isolated by extraction with a polar organic solvent which is not infinitely miscible with water, the pH of the reaction solution being increased, before or during the extraction, by adding a base.

* * * * *